United States Patent [19]

Asahi et al.

[11] Patent Number: 5,036,108

[45] Date of Patent: Jul. 30, 1991

[54] WATER-IN-OIL EMULSION COSMETIC

[75] Inventors: Masahiko Asahi, Tokyo; Noriko Shirakawa, Kanagawa; Yuko Kikuta, Tokyo, all of Japan

[73] Assignee: Kao Corporation, Tokyo, Japan

[21] Appl. No.: 450,149

[22] Filed: Dec. 13, 1989

[30] Foreign Application Priority Data

Dec. 14, 1988 [JP] Japan .................................. 63-315694
Feb. 15, 1989 [JP] Japan ...................................... 1-35515

[51] Int. Cl.$^5$ ....................... A61K 7/021; A61K 7/48; A61K 9/08; A61K 9/10
[52] U.S. Cl. ...................................... 514/937; 424/59; 424/63; 424/69; 514/844; 514/845; 514/847; 514/938; 514/941
[58] Field of Search ............... 514/772, 844, 938, 940, 514/937

[56] References Cited

U.S. PATENT DOCUMENTS

| | | | |
|---|---|---|---|
| 3,489,690 | 1/1970 | Lachampt et al. | 424/59 X |
| 3,666,671 | 5/1972 | Kalopissis et al. | 424/59 |
| 4,199,599 | 4/1980 | Klein | 424/59 |
| 4,254,104 | 3/1981 | Suzuki | 514/938 |
| 4,425,329 | 1/1984 | Tsutsumi et al. | 514/844 |
| 4,479,887 | 10/1984 | Seibert | 514/938 |
| 4,543,258 | 9/1985 | Urata et al. | 514/938 |
| 4,776,976 | 11/1988 | Nakamura et al. | 514/938 X |

Primary Examiner—Dale R. Ore
Attorney, Agent, or Firm—Sughrue, Mion, Zinn, Macpeak & Seas

[57] ABSTRACT

A water-in-oil type emulsion cosmetic, which comprises a specific emulsifier mixture, an oily base containing a silicone oil and water and has a viscosity of 20,000 cps or below at 25° C. is disclosed. The water-in-oil type emulsion cosmetic of the present invention imparts a good feel to the skin during use, is safe to use and has a high storage stability, which makes it widely applicable for use in, for example, milky lotions, body-care lotions and liquid-type foundations.

10 Claims, No Drawings

WATER-IN-OIL EMULSION COSMETIC

FIELD OF THE INVENTION

This invention relates to a water-in-oil type emulsion cosmetic. More particularly, it relates to a water-in-oil type emulsion cosmetic which comprises a specific emulsifier mixture, an oily base containing a silicone oil and water, which imparts a good feel to the skin during and after use, is safe to use, and has a high storage stability.

BACKGROUND OF THE INVENTION

Water-in-oil type emulsion cosmetics have been frequently applied to skin-care products and make-up products, since they have a high resistance to microorganisms, form an oily film on the surface of the skin so as to prevent the vaporization of moisture, have a high water repellency and scarcely cause deterioration in make-up, as compared with oil-in-water type cosmetics. However, water-in-oil type emulsion cosmetics are disadvantageous in that a continuous oily phase, which is present, restricts the stable amount of the moisture present, which results in an intense oily feel or a serious stickiness upon application to the skin. In order to solve these problems, JP-B-60-26366 (the term "JP-B" as used herein means an "examined Japanese Patent Publication") (corresponding to U.S. Pat. No. 4,425,329) discloses a water-in-oil type emulsion cosmetic containing a large amount of moisture which comprises mixed emulsifiers including α-monoglyceryl ether. Although this cosmetic has an overall high viscosity which enables it to maintain a large stable amount of water which produces little oily feel or stickiness to the skin, the spreadability thereof is considerably poor.

On the other hand, silicones are known as oily bases which are excellent in lubricating properties and water repellency. Recently, volatile silicones have been frequently employed in particular, since they show a good spreadability upon application and scarcely bring about any deterioration in make-up. However, it is very difficult to obtain a highly stable water-in-oil type emulsion cosmetic which comprises a silicone oil as a base.

Accordingly, it has been urgently required to develop a water-in-oil type emulsion cosmetic which has an excellent spreadability, is safe to use, and a high safety and comprises a large stable amount of moisture (water).

SUMMARY OF THE INVENTION

Under these circumstances, we have conducted extensive studies and have consequently found out that a safe water-in-oil type emulsion cosmetic in the form of an emulsion having a high storage stability, which imparts a good feel to the skin during and after use can be obtained by controlling the viscosity of a water-in-oil type emulsion cosmetic comprising an oily base containing a silicone oil and emulsifying the oily base and water with the use of a specific emulsifier mixture to thereby give a water-in-oil type emulsion, thus completing the present invention.

Accordingly, the present invention provides a water-in-oil type emulsion cosmetic which comprises an oily base containing a silicone oil, water and an emulsifier and has a viscosity at 25° C. of 20,000 cps or below.

DETAILED DESCRIPTION OF THE INVENTION

The viscosity of the cosmetic of the present invention is measured by a B-type viscometer under the condition of which the cosmetic was stirred by using a Rotor No. 4 at a rotation ratio of 6 rpm at 25° C. for 1 minute.

When the viscosity of the cosmetic of the present invention exceeds 20,000 cps, the water-in-oil type emulsion cosmetic imparts a poor spreadability and thus the object of the present invention cannot be achieved. When the viscosity thereof is excessively low, on the other hand, the water-in-oil type emulsion cosmetic shows a poor adhesion to the skin. Thus the viscosity preferably ranges from 2,000 to 15,000 cps.

The silicone oil used in the present invention include those commonly employed in cosmetics. Examples thereof include dimethyl polysiloxane, dimethyl cyclopolysiloxane, methylphenyl polysiloxane and methylhydrodiene polysiloxane. In order to lower the oily feel and stickiness to the skin, volatile dimethyl polysiloxane or dimethyl cyclopolysiloxane are preferably used. Either one of these materials or a mixture thereof may be used. The silicone oil may be present in any weight percent (i.e., 50% by weight or more, or less than 50% by weight). Examples of other oily bases include hydrocarbons such as squalane, liquid paraffin and vaseline, waxes such as sperm whale and carnauba wax, esters such as jojoba oil, octyldodecyl myristate and neopentyl glycol dioctanate, natural animal and vegetable fats and oils such as olive oil and macadamia nut oil and diglycerides. Either one of these materials or a mixture thereof may be used. The oily base may be used in an amount of from 25 to 45% by weight based on the total weight of the cosmetic.

The emulsifiers to be used in the present invention, for example, when an oily base containing 50% by weight or more of a silicone oil is used, include the mixed emulsifiers (a) comprising the following components (1), (2), (3) and (4) which are preferable:

(1) 15 to 35% by weight α-monoglyceryl ethers represented by the following general formula (I):

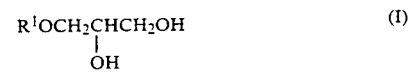

wherein $R^1$ represents a straight-chain or branched alkyl or alkenyl group having 10 to 24 carbon atoms;

(2) 20 to 70% by weight of at least dimethyl polysiloxane/polyoxyalkylene copolymers represented by the following general formula (II):

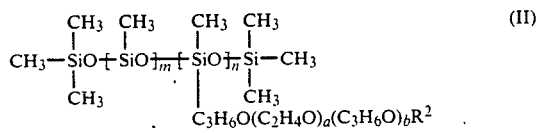

wherein $R^2$ represents a hydrogen atom or an alkyl group having 1 to 5 carbon atoms;

m is an integer of 1 to 150;

n is an integer of 1 to 50; and a and b, which may be the same or different, are 0 or an integer of 1 to 35;

(3) 1 to 20% by weight of a polyvalent metal salt of a saturated or unsaturated fatty acid having 10 to 22 carbon atoms; and (4) 5 to 50% by weight of an inorganic salt having a solubility in water at 20° C. of 0.2 g/100 g of water or more.

It is particularly preferred that the emulsifier (a) is the mixed emulsifier comprising 20 to 30% by weight of the α-monoglyceryl ethers represented (I) above, 40 to 60% by weight of the dimethyl polysiloxane/polyoxyalkylene copolymer described above in (2), 1 to 10% by weight of the polyvalent metal salt of the saturated or unsaturated fatty acid described above in (3), and 10 to 30% by weight of the inorganic salt described above in (4).

The emulsifier to be used in the present invention, when an oily base containing less than 50% by weight of a silicone oil is used, include the following mixed emulsifiers (b) comprising the following components (1), (3), (4) and (5) which are preferable:

(1) 15 to 35% by weight of the α-monoglyceryl ethers represented by general formula (I) above;

(3) 1 to 20% by weight of the polyvalent metal salt of the saturated or unsaturated fatty acid described above in (3);

(4) 5 to 50% by weight of the inorganic salt described above in (4); and (5) 35 to 65% by weight of one or more nonionic surfactants having a HLB (hydrophilic-lipophilic balance) of 6.0 to 10.5.

It is particularly preferred that the emulsifier (b) is the mixed emulsifier comprising 20 to 30% by weight of the α-monoglyceryl ethers represented by general formula (I) above, 1 to 10% by weight of the polyvalent metal salt of the saturated or unsaturated fatty acid described above in (3), 10 to 30% by weight of the inorganic salt described above in (4), and 40 to 60% by weight of the nonionic surfactant described above in (5).

Among the components of the mixed emulsifiers (a) or (b), examples of the α-monoglyceryl ether, i.e., component (1), include those represented by the formula (I) wherein $R^1$ is a straight-chain alkyl group having 10 to 24 carbon atoms such as a lauryl, myristyl, cetyl, stearyl, eicosyl or dococyl group; a straight-chain alkenyl group having 10 to 24 carbon atoms such as an oleyl group; and a branched alkyl group having 10 to 24 carbon atoms and having a side chain at the β-position such as a 5,7,7-trimethyl-2-(1,3,3-trimethylbutyl)octyl, 2-heptylundecyl, 2-hexyldecyl or 2-octyldodecyl group. Among these materials, those wherein $R^1$ is a straight-chain alkyl group or branched alkyl group having 16 to 22 carbon atoms are particularly preferable. Any one of these α-monoglyceryl ethers or a mixture thereof may be used.

Either one dimethyl polysiloxane/polyoxyalkylene copolymer or a mixture thereof may be used as component (2). It is particularly preferable to combine a copolymer represented by the general formula (II) wherein $R^2$ is a hydrogen atom, m is an integer ranging from 20 to 30, n is an integer ranging from 2 to 5, a is an integer ranging from 2 to 5 and b is 0 with another copolymer represented by the general formula (II) wherein $R^2$ is a methyl group, m is an integer ranging from 4 to 10, n is an integer ranging from 1 to 6, a is 0 and b is an integer ranging from 7 to 13. Suitable examples of the former and the latter are "Silicone KF-945A", trade name, available from The Shin-Etsu Chemical Co., Ltd. and "NUC Silicone FZ-2110", trade name, available from Nippon Unica Co., Ltd., respectively. These materials may be appropriately used at a mixing ratio of from 2:1 to 1:2 by weight.

As the polyvalent metal salt of a fatty acid which is component (3), those having 12 to 18 carbon atoms are more preferable. Examples thereof include calcium, magnesium, zinc and aluminum salts. Among these salts, aluminum salts are preferable. Thus, preferable examples of the fatty acid polyvalent metal salt include aluminum monostearate, aluminum distearate, aluminum monooleate, aluminum monopalmitate and aluminum monolaurate.

Examples of the inorganic salt, namely, component (4), include magnesium sulfate, potassium sulfate, sodium sulfate, aluminum sulfate, magnesium nitrate, potassium nitrate, sodium nitrate, aluminum nitrate, magnesium chloride, potassium chloride, sodium chloride and aluminum chloride. Among these materials, magnesium sulfate, potassium sulfate, magnesium chloride, potassium chloride and aluminum chloride are particularly preferable.

As the nonionic surfactant, namely, component (5), other than α-monoglyceryl ether, any nonionic surfactants which have a HLB value (hydrophilic-lipophilic balance) of from 6.0 to 10.5 can be used.

The HLB value of the surfactants can be calculated, for example, as follows:

The HLB value of a polyhydric alcohol fatty acid ester is calculated by the following equation:

$$HLB\ value = 20(1 - S/A)$$

where S is a saponification value of the ester and A is a neutralization value of the fatty acid.

The HLB value of a polyoxyethylene nonionic surfactant is calculated by the following equation:

$$HLB\ value = E/5$$

where E is a value of percent by weight of an ethylene oxide group moiety.

In addition, a mixture of two or more nonionic surfactants capable of having a HLB value ranging from 6.0 to 10.5 can be used, even though one or more of these surfactants alone cannot give a HLB value falling within the above range. In the this case, the HLB value of the mixture may be calculated as the weighted average of the surfactants constituting the mixture. Table 1 shows examples thereof.

TABLE 1

| | HLB value |
|---|---|
| Surfactant having a HLB of less than 6: | |
| Sorbitan fatty acid ester | |
| Sorbitan monostearate | 4.7 |
| Sorbitan tristearate | 2.1 |
| Sorbitan monooleate | 4.3 |
| Sorbitan trioleate | 1.8 |
| Glyceryl fatty acid ester | |
| Glycerol monostearate | 3.5 |
| Glycerol monooleate | 2.8 |
| Surfactant having a HLB of from 6 to 10.5: | |
| Polyoxyethylene-hardened castor oil | |
| POE (5)-hardened castor oil | 6.0 |
| POE (7.5)-hardened castor oil | 6.0 |
| POE (10)-hardened castor oil | 6.5 |
| POE (20)-hardened castor oil | 10.5 |
| Polyoxyethylene sorbitan fatty acid ester | |
| POE (6) sorbitan monostearate | 9.6 |
| POE (20) sorbitan tristearate | 10.5 |
| POE (6) sorbitan monooleate | 10.0 |
| Surfactant having a HLB of 6 to 10.5: | |
| Polyoxyethylene alkyl ether | |
| POE (4-6) lauryl ether | 9.6-10.5 |

TABLE 1-continued

| | HLB value |
|---|---|
| POE (6) stearyl ether | 9.4 |
| POE (4-8) oleyl ether | 8.8-10.0 |
| Surfactant having a HLB of more than 10.5: | |
| *Polyoxyethylene-hardened castor oil* | |
| POE (30)-hardened castor oil | 11.0 |
| POE (40)-hardened castor oil | 12.5 |
| POE (50)-hardened castor oil | 13.5 |
| POE (60)-hardened castor oil | 14.0 |
| *Polyoxyethylene sorbitan fatty acid ester* | |
| POE (6) sorbitan trioleate | 11.0 |
| POE (6) sorbitan monolaurate | 13.3 |
| POE (20) sorbitan monostearate | 14.9 |
| *Polyoxyethylene alkyl ether* | |
| POE (8-20) lauryl ether | 12-15 |
| POE (20) stearyl ether | 13.9 |
| POE (9) oleyl ether | 12.0 |
| *Polyoxyethylene fatty acid ester* | |
| Polyethylene glycol (600) monostearate | 13.4 |

In the above table, "POE" means polyoxyethylene, each value in parentheses means the average added mole number in the case of POE or the average molecular weight in the case of polyethylene glycol.

In the present invention, the emulsifier can be preferably used in an amount of from 1 to 10% by weight of the whole cosmetic, when the content of the emulsifier is less than 1% by weight, the water-in-oil type emulsion cosmetic of the present invention cannot be stabilized. When it exceeds 10% by weight, on the other hand, the whole system becomes highly viscous, which brings about a poor spreadability and a serious oily feel and stickiness to the skin, thus resulting in an undesirable cosmetic.

Although the water-in-oil type emulsion cosmetic of the present invention may contain an arbitrary amount of water, the content of water including other water soluble solvent(s) may preferably range from 34 to 74% by weight of the whole cosmetic, more preferably from 50% by weight or above of the whole cosmetic, in order to impart an excellent feel to the skin during use, namely, a high spreadability and little oily feel or stickiness to the skin. Other water soluble solvents include lower alcohols such as ethanol, glycerol, sorbitol, propylene glycol and 1,3-butylene glycol and polyols.

The water-in-oil type emulsion cosmetic of the present invention may further contain other components commonly used in cosmetics in an amount of from 0 to 40% by weight, so long as the effects of the present invention are not damaged thereby. Examples of these components include powders, humectants, intercellular substances such as ceramide, UV absorbers, alcohols, chelates, pH controllers, preservatives, thickeners, colorants and perfumes.

Among these materials, powders may be used in an amount of from 10 to 40% by weight, preferably from 15 to 30% by weight, based on the whole cosmetic to thereby give a milky foundation. As the powder, those commonly employed in cosmetics, for example, extender pigments such as talc, mica, kaolin and sericite, inorganic pigments such as titanium oxide, zinc oxide and ultramarine iron oxide and organic pigments such as titanium mica pearl pigments, blue colorant No.404, red colorant No.202 and yellow colorant No.401 may be used. In the present invention, one or more of these powders can be arbitrarily employed.

The cosmetic of the present invention may be in the form of, for example, an emulsion such as a milky lotion or a body care milky lotion or a liquid-type foundation. These products may be produced from the above-mentioned materials in a conventional manner.

As described above, the water-in-oil type emulsion cosmetic of the present invention has the advantages of conventional oil-in-water type emulsion cosmetics as well as having a low viscosity and a high moisture content. Thus, it is highly spreadable and exerts a prolonged make-up effect while imparting little oily feel or stickiness to the skin.

To further illustrate the present invention, and not by way of limitation, the following Examples are given.

EXAMPLE 1

Milky lotions of the compositions shown in Table 2 were produced and the emulsion stability, viscosity and feel to the skin during use of each product were evaluated. Table 2 summarizes the results.

TABLE 2

| Component | Comparative Product 1-1 (% by weight) | Comparative Product 1-2 (% by weight) | Comparative Product 1-3 (% by weight) | Product of Invention 1-1 (% by weight) |
|---|---|---|---|---|
| (1) α-Monooleyl glyceryl ether | 2.0 | — | — | 1.0 |
| (2) Glyceryl monooleate | — | — | 1.0 | — |
| (3) Dimethyl polysiloxane/polyoxyalkylene copolymer* | — | 2.0 | 2.0 | 1.0 |
| (4) Dimethyl polysiloxane/polyoxyalkylene copolymer** | 1.0 | 1.0 | 1.0 | 1.0 |
| (5) Aluminum distearate | 0.2 | 0.2 | 0.2 | 0.2 |
| (6) Squalane | 5.0 | 5.0 | 5.0 | 5.0 |
| (7) Dimethyl polysiloxane (6cs) | 6.0 | 6.0 | 6.0 | 6.0 |
| (8) Octamethyl cyclotetrasiloxane | 15.0 | 15.0 | 15.0 | 15.0 |
| (9) Dioctanic neopentyl glycol | 3.0 | 3.0 | 3.0 | 3.0 |
| (10) Magnesium sulfate | 0.7 | 0.7 | 0.7 | 0.7 |
| (11) Glycerol | 5.0 | 5.0 | 5.0 | 5.0 |
| (12) Methylparaben | 0.1 | 0.1 | 0.1 | 0.1 |
| (13) Perfume | 0.1 | 0.1 | 0.1 | 0.1 |
| (14) Water | balance | balance | balance | balance |
| Total | 100.0 | 100.0 | 100.0 | 100.0 |

Notes:
*In formula (II), $R^2$ is H, m is 20 to 30, n is 2 to 5, a is 2 to 5 and b is 0.
**In formula (II), $R^2$ is $CH_3$, m is 4 to 10, n is 1 to 6, a is 0 and b is 7 to 13.

PRODUCTION

Magnesium sulfate, methylparaben and glycerol were added to water and heated. The aqueous phase thus obtained was maintained at 70° C. The remaining components were made molten by heating and the oily phase thus obtained was heated to 70° C. Next, the aqueous phase was added to the oily phase and the mixture was emulsified in an emulsifying machine. The resulting emulsion was cooled to a final temperature of 30° C. in a heat exchanger to thereby give a milky lotion (the product of the invention 1-1). This procedure was repeated except varying the composition so as to give the comparative products 1-1, 1-2 and 1-3. The results are shown in Table 3 below.

The above aqueous phase was mixed upon heating and then maintained at 70° C. The oily phase was made molten and dispersed at 70° C. The aqueous phase was added to the oily phase and emulsified in an emulsifying machine. The resulting emulsion was cooled to a final temperature of 30° C. in a heat exchanger to thereby give a body-care milky lotion (the product of the invention 1-2).

EXAMPLE 3

TABLE 3

| | Emulsion Stability[1] | | | | | Feel to the skin during use[3] | | |
|---|---|---|---|---|---|---|---|---|
| | Immediately after | After 1 month | | | Viscosity[2] (cps) | Spreadability | Stickness | Sustained make-up |
| | | −5° C. | Room Temperature | 40° C. | | | | |
| Comparative Product 1-1 | ○ | | | | 100,000 or more | | Δ | Δ |
| Comparative Product 1-2 | ○ | ○ | ○ | Δ | 100,000 or more | | Δ | Δ |
| Comparative Product 1-3 | ○ | ○ | ○ | | 100,000 or more | | Δ | Δ |
| Product of Invention 1-1 | ○ | ○ | ○ | ○ | 5,800 | ○ | ○ | ○ |

Criteria:
[1] ○: No separation or agglomeration.
Δ: Slight separation and agglomeration.
×: Separation and agglomeration.
[2] Determined with a B type viscometer (model B8L, manufactured by Tokyo Keiki K. K.) at 25° C.
[3] Practical evaluation by ten skilled panelists.
○: 7 or more panelists, among 10, felt good.
Δ: 4 to 6 panelists, among 10, felt good.
×: 3 or less panelists, among 10, felt good.

The above Table 3 obviously indicates that the product of the invention 1-1 having a lower viscosity is superior to the comparative products 1-1 to 1-3 in stability and feel to the skin during use including spreadability, stickiness and sustained makeup effect.

EXAMPLE 2

| Body-care milky lotion: | |
|---|---|
| | (% by weight) |
| Oily phase: | |
| liquid paraffin | 3.0 |
| dimethyl polysiloxane (6cs) | 5.0 |
| octamethyl cyclotetrasiloxane | 20.0 |
| spherical polymethyl silsesquioxane | 2.0 |
| α-monooleyl glyceryl ether | 1.0 |
| dimethyl polysiloxane/polyoxyalkylene copolymer* | 1.0 |
| dimethyl polysiloxane/polyoxyalkylene copolymer** | 0.5 |
| aluminum monostearate | 0.1 |
| Aqueous phase: | |
| magnesium chloride | 0.4 |
| glycerol | 2.0 |
| methylparaben | 0.1 |
| perfume | 0.1 |
| ethanol | 5.0 |
| water | balance |
| Total | 100.0 |

Notes:
*The same as the one used in Example 1.
**In formula (II), $R^2$ is $CH_3$, m is 15 to 25, n is 2 to 4, a is 25 to 35 and b is 10 to 20.

| Hand lotion: | |
|---|---|
| | (% by weight) |
| Oil phase: | |
| liquid paraffin | 10.0 |
| methylphenyl polysiloxane | 5.0 |
| decamethyl cyclopentasiloxane | 15.0 |
| α-monoisostearyl glyceryl ether | 1.0 |
| dimethyl polysiloxane/polyoxyalkylene copolymer* | 0.5 |
| dimethyl polysiloxane/polyoxyalkylene copolymer** | 1.0 |
| aluminum monooleate | 1.0 |
| Aqueous phase: | |
| potassium sulfate | 2.5 |
| glycerol | 10.0 |
| 70% aqueous solution of sorbitol | 15.0 |
| methylparaben | 0.1 |
| perfume | 0.1 |
| water | balance |
| Total | 100.0 |

Notes:
*In formula (II), $R^2$ is H, m is 5 to 100, n is 1 to 5, a is 7 to 15 and b is 0.
**The same as the one used in Example 1.

With the use of the above materials, the procedure of Example 2 was repeated to thereby give a hand lotion (the product of the invention 1-3).

EXAMPLE 4

| Sun-care lotion | (% by weight) |
|---|---|
| Oily phase: | |
| dimethyl polysiloxane (6cs) | 10.0 |
| decamethyl cyclopentasiloxane | 20.0 |
| α-monopalmitooleyl glyceryl ether | 1.0 |
| dimethyl polysiloxane/polyoxyalkylene copolymer* | 1.0 |
| dimethyl polysiloxane/polyoxyalkylene copolymer** | 1.0 |
| aluminum monostearate | 0.2 |
| octyl methoxycinnamate | 3.0 |
| oxybenzone | 0.5 |
| Aqueous phase: | |
| potassium chloride | 0.7 |
| glycerol | 2.0 |
| 1,3-butylene glycol | 2.0 |
| methylparaben | 0.1 |
| perfume | 0.1 |
| water | balance |
| Powder component (hydrophobic treated): | |
| titanium oxide | 3.0 |
| Total | 100.0 |

Notes:
*In formula (II), $R^2$ is H, m is 5 to 15, n is 2 to 5, a is 2 to 5 and b is 0.
**In formula (II), $R^2$ is $CH_3$, m is 60 to 80, n is 3 to 8, a is 15 to 25 and b is 25 to 35.

The above aqueous phase was mixed upon heating and then maintained at 70° C. The oily phase was made molten at 70° C. and then the powder component was dispersed therein. The aqueous phase was added to the oily phase/powder and emulsified in an emulsifying machine. The resulting emulsion was cooled to a final temperature of 30° C. in a heat exchanger to thereby give a sun-care milky lotion (the product of the invention (1-4).

EXAMPLE 5

| Liquid-type emulsified foundation: | (% by weight) |
|---|---|
| Oily phase: | |
| squalane | 4.0 |
| dimethyl polysiloxane (6cs) | 5.0 |
| dioctanic neopentyl glycol | 3.0 |
| myristic isostearic diglyceride | 2.0 |
| octamethyl cyclotetrasiloxane | 12.0 |
| decamethyl cyclopentasiloxane | 3.0 |
| α-monoisostearyl glyceryl ether | 1.0 |
| dimethyl polysiloxane/polyoxyalkylene copolymer* | 1.0 |
| dimethyl polysiloxane/polyoxyalkylene copolymer** | 1.0 |
| aluminum distearate | 0.2 |
| Aqueous phase: | |
| magnesium sulfate | 0.7 |
| glycerol | 3.0 |
| methylparaben | 0.1 |
| perfume | 0.1 |
| water | balance |
| Powder component (hydrophobic treated): | |
| titanium oxide | 5.0 |
| sericite | 2.0 |
| talc | 3.0 |
| red oxide | 0.4 |
| yellow iron oxide | 0.7 |
| black iron oxide | 0.1 |
| Total | 100.0 |

Notes:
*The same as the one used in Example 1.
**The same as the one used in Example 1.

With the use of the above materials, the procedure of Example 4 was repeated to thereby give a liquid-type emulsion foundation (the product of the invention 1-5).

Each of the products of the invention 1-2 to 1-5 produced in the above Examples 1 to 5 was a water-in-oil type emulsion cosmetic which showed a viscosity of 20,000 cps or lower, a high stability and a good feel upon use.

EXAMPLE 6

Milky lotions of the compositions shown in Table 4 were produced and the emulsion stability, viscosity and feel upon use of each product were evaluated. Table 5 summarizes the results. Production:

Magnesium sulfate, methylparaben and glycerol were added to water and heated. The aqueous phase thus obtained was maintained at 70° C. The residual components were molten upon heating and the resulting oily phase was similarly heated to 70° C. Next, the aqueous phase was added to the oily phase and emulsified in an emulsifying machine. The resulting emulsion was cooled to 30° C. in a heat exchanger to thereby give a milky lotion (the product of the invention 2-1). This procedure was repeated except changing the composition so as to give the comparative products 2-1, 2-2 and 2-3.

TABLE 4

| Component | Comparative Product 2-1 (% by weight) | Comparative Product 2-2 (% by weight) | Comparative Product 2-3 (% by weight) | Product of Invention 2-1 (% by weight) |
|---|---|---|---|---|
| (1) α-Monooleyl glyceryl ether | 2.0 | — | — | 1.0 |
| (2) Glyceryl monooleate | — | — | 1.0 | — |
| (3) Polyoxyalkylene (20)-hardened castor oil (HLB 10.5)* | — | 2.0 | 2.0 | 1.0 |
| (4) Sorbitan sesquiisostearate (HLB 4.5)* | 1.0 | 1.0 | 1.0 | 1.0 |
| (5) Aluminum distearate | 0.2 | 0.2 | 0.2 | 0.2 |
| (6) Squalane | 15.0 | 15.0 | 15.0 | 15.0 |
| (7) Liquid paraffin | 6.0 | 6.0 | 6.0 | 6.0 |
| (8) Octamethyl cyclotetrasiloxane | 5.0 | 5.0 | 5.0 | 5.0 |
| (9) Dioctanic neopentyl glycol | 3.0 | 3.0 | 3.0 | 3.0 |
| (10) Magnesium sulfate | 0.7 | 0.7 | 0.7 | 0.7 |
| (11) Glycerol | 5.0 | 5.0 | 5.0 | 5.0 |
| (12) Methylparaben | 0.1 | 0.1 | 0.1 | 0.1 |
| (13) Perfume | 0.1 | 0.1 | 0.1 | 0.1 |
| (14) Water | balance | balance | balance | balance |

TABLE 4-continued

| Component | Comparative Product 2-1 (% by weight) | Comparative Product 2-2 (% by weight) | Comparative Product 2-3 (% by weight) | Product of Invention 2-1 (% by weight) |
|---|---|---|---|---|
| Total | 100.0 | 100.0 | 100.0 | 100.0 |

Note: *The HLB value of the mixture of components (3) and (4) was 7.5.

TABLE 5

| | Emulsion Stability[1] | | | | | Feel to the skin during use[3] | | |
|---|---|---|---|---|---|---|---|---|
| | Immediately after | After 1 month | | | Viscosity[2] (cps) | Spread-ability | Stickness | Sustained make-up |
| | | −5° C. | Room Temperature | 40° C. | | | | |
| Comparative Product 2-1 | ○ | | | | 100,000 or more | | Δ | Δ |
| Comparative Product 2-2 | ○ | ○ | ○ | Δ | 100,000 or more | | Δ | Δ |
| Comparative Product 2-3 | ○ | ○ | ○ | | 100,000 or more | | Δ | Δ |
| Product of Invention 2-1 | ○ | ○ | ○ | ○ | 7,000 | ○ | ○ | ○ |

Criteria:
[1] ○: No separation or agglomeration.
Δ: Slight separation and agglomeration.
: Separation and agglomeration.
[2] Determined with a B type viscometer (model B8L, manufactured by Tokyo Keiki K. K.) at 25° C.
[3] Practical evaluation by ten skilled panelists.
○: 7 or more panelists, among 10, felt good.
Δ: 4 to 6 panelists, among 10, felt good.
: 3 or less panelists, among 10, felt good.

The above Table 5 obviously indicates that the produce of the invention 2-1 having a lower viscosity is superior to the comparative products 2-1 to 2-3 in stability and feel to the skin during use including spreadability, stickiness and sustained make-up effect.

EXAMPLE 7

| Body-care milky lotion: | (% by weight) |
|---|---|
| Oily phase: | |
| (1) liquid paraffin | 3.0 |
| (2) squalane | 20.0 |
| (3) octamethyl cyclotetrasiloxane | 5.0 |
| (4) spherical polymethyl silsesquioxane | 2.0 |
| (5) α-monooleyl glyceryl ether | 1.0 |
| (6) polyoxyethylene (20)-hardened castor oil (HLB 10.5) | 1.0 |
| (7) aluminum monostearate | 0.1 |
| Aqueous phase: | |
| (8) magnesium chloride | 0.4 |
| (9) glycerol | 2.0 |
| (10) methylparaben | 0.1 |
| (11) perfume | 0.1 |
| (12) ethanol | 5.0 |
| (13) water | balance |
| Total | 100.0 |

The above aqueous phase was mixed upon heating and then maintained at 70° C. The oily phase was made molten at 70° C. The aqueous phase was added to the oily phase and emulsified in an emulsifying machine. The resulting emulsion was cooled to a final temperature of 30° C. in a heat exchanger to thereby give a body-care milky lotion (the product of the invention 2-2).

EXAMPLE 8

| Hand lotion: | (% by weight) |
|---|---|
| Oily phase: | |
| (1) liquid paraffin | 10.0 |
| (2) squalane | 15.0 |
| (3) decamethyl cyclopentasiloxane | 5.0 |
| (4) α-monoisostearyl glyceryl ether | 1.0 |
| (5) polyoxyethylene (40)-hardened castor oil (HLB 12.5)* | 0.5 |
| (6) glycerol monostearate (HLB 3.5)* | 1.0 |
| (7) aluminum monooleate | 1.0 |
| Aqueous phase: | |
| (8) potassium sulfate | 2.5 |
| (9) glycerol | 10.0 |
| (10) 70% aqueous solution of sorbitol | 15.0 |
| (11) methylparaben | 0.1 |
| (12) perfume | 0.1 |
| (13) water | balance |
| Total | 100.0 |

*The HLB value of the mixture of components (5) and (6) was 6.5.

With the use of the above materials, the procedure of Example 7 was repeated to thereby give a hand lotion (the product of the invention 2-3).

EXAMPLE 9

| Sun-care lotion: | (% by weight) |
| --- | --- |
| Oily phase: | |
| (1) liquid paraffin | 20.0 |
| (2) decamethyl cyclopentasiloxane | 10.0 |
| (3) α-monopalmitoyloleyl glyceryl ether | 1.0 |
| (4) polyoxyethylene (60)-hardened castor oil (HLB 14.0)* | 1.0 |
| (5) glycerol monooleate (HLB 2.8)* | 1.0 |
| (6) aluminum monostearate | 0.2 |
| (7) octyl methoxycinnamate | 3.0 |
| (8) oxybenzone | 0.5 |
| Aqueous phase: | |
| (9) potassium chloride | 0.7 |
| (10) glycerol | 2.0 |
| (11) 1,3-butylene glycol | 2.0 |
| (12) methylparaben | 0.1 |
| (13) perfume | 0.1 |
| (14) water | balance |
| Powder component (hydrophobic treated): | |
| (15) titanium oxide | 3.0 |
| Total | 100.0 |

Note: *The HLB value of the mixture of components (4) and (5) was 8.4.

The above aqueous phase was mixed upon heating and then maintained at 70° C. The oily phase was made molten at 70° C. and then the powder component was dispersed therein. The aqueous phase was added to the oily phase/powder and emulsified in an emulsifying machine. The resulting emulsion was cooled to a final temperature of 30° C. in a heat exchanger to thereby give a sun-care milky lotion (the product of the invention 2-4).

EXAMPLE 10

| Liquid-type emulsion foundation: | (% by weight) |
| --- | --- |
| Oily phase: | |
| (1) squalane | 4.0 |
| (2) liquid paraffin | 7.0 |
| (3) dioctanic neopentyl glycol | 3.0 |
| (4) myristic isostearic diglyceride | 2.0 |
| (5) octamethyl cyclotetrasiloxane | 10.0 |
| (6) decamethyl cyclopentasiloxane | 3.0 |
| (7) α-monoisostearyl glyceryl ether | 1.0 |
| (8) polyoxyethylene (60)-hardened castor oil (HLB 14.0)* | 1.0 |
| (9) sorbitan sesquiisostearate (HLB 4.5)* | 1.0 |
| (10) aluminum distearate | 0.2 |
| Aqueous phase: | |
| (11) magnesium sulfate | 0.7 |
| (12) glycerol | 3.0 |
| (13) methylparaben | 0.1 |
| (14) perfume | 0.1 |
| (15) water | balance |
| Powder component (hydrophobic treated): | |
| (16) titanium oxide | 5.0 |
| (17) sericite | 2.0 |
| (18) talc | 3.0 |
| (19) red oxide | 0.4 |
| (20) yellow iron oxide | 0.7 |
| (21) black iron oxide | 0.1 |
| Total | 100.0 |

*The HLB value of the mixture of components (8) and (9) was 9.3.

With the use of the above materials, the procedure of Example 9 was repeated to thereby give a liquid-type emulsion foundation (the product of the invention 2-5).

Each of the products of the invention 2-2 to 2-5 produced in the above Examples 7 to 10 was a water-in-oil type emulsion cosmetic which showed a viscosity of 20,000 cps or lower, a high stability and imparted a good feel to the skin during use.

What is claimed is:

1. A water-in-oil emulsion cosmetic which comprises an oily base containing a silicone oil, water and an emulsifier and has a viscosity of 20,000 cps or below at 25° C., wherein said oily base contains the silicone oil in an amount of 50% by weight or more, and said emulsifier is an emulsifier mixture comprising the following components (1) to (4):

(1) 15 to 35% by weight of at least one α-monoglyceryl ether represented by the following formula (I):

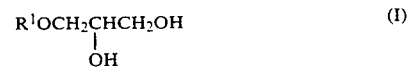

wherein $R^1$ represents a straight-chain or branched alkyl or alkenyl group having 10 to 24 carbon atoms;

(2) 20 to 70% by weight of at least one dimethyl polysiloxane/polyoxyalkylene copolymer represented by the following formula (II):

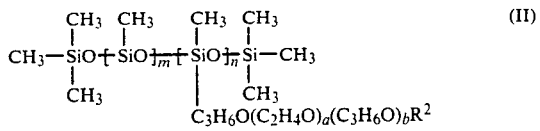

wherein $R^2$ represents a hydrogen atom or an alkyl group having 1 to 5 carbon atoms; m is an integer of from 1 to 150; n is an integer of from 1 to 50; and a and b, which may be the same or different, are each 0 or an integer of from 1 to 35;

(3) 1 to 20% by weight of a polyvalent metal salt of a saturated or unsaturated fatty acid having 10 to 22 carbon atoms; and (4) 5 to 50% by weight of an inorganic salt having a solubility in water at 20° C. of 0.2 g/100 g of water or more.

2. The water-in-oil emulsion cosmetic as claimed in claim 1, wherein said emulsifier is an emulsifier mixture comprising 20 to 30% by weight of said α-monoglyceryl ether represented by said formula (I), 40 to 60% by weight of said dimethyl polysiloxane/polyoxyalkylene copolymer, 1 to 10% by weight of said polyvalent metal salt of the saturated or unsaturated fatty acid, and 10 to 30% by weight of said inorganic salt.

3. The water-in-oil emulsion cosmetic as claimed in claim 1, wherein said polyvalent metal salt is at least one salt selected from the group consisting of calcium, magnesium, zinc and aluminum salts.

4. The water-in-oil emulsion cosmetic as claimed in claim 1, wherein said inorganic salt is at least one salt selected from the group consisting of magnesium sulfate, potassium sulfate, sodium sulfate, aluminum sulfate, magnesium nitrate, potassium nitrate, sodium nitrate, aluminum nitrate, magnesium chloride, potassium chloride, sodium chloride and aluminum chloride.

5. The water-in-oil emulsion cosmetic as claimed in claim 1, wherein said oily base further contains at least one compound selected from the group consisting of hydrocarbons, waxes, esters, natural animal and vegetable fats and oils and diglycerides.

6. A water-in-oil emulsion cosmetic which comprises an oily base containing a silicone oil, water and an emulsifier and has a viscosity of 20,000 cps or below at 25° C., wherein said oily base contains the silicone oil in an amount of less than 50% by weight, and said emulsifier is an emulsifier mixture comprising the following components (1), (3), (4) and (5):

(1) 15 to 35% by weight of at least one α-monoglyceryl ether represented by the following formula (I):

wherein $R^1$ represents a straight-chain or branched alkyl or alkenyl group having 10 to 24 carbon atoms;

(3) 1 to 20% by weight of a polyvalent metal salt of a saturated or unsaturated fatty acid having 10 to 22 carbon atoms;

(4) 5 to 50% by weight of an inorganic salt having a solubility in water at 20° C. of 0.2 g/100 g of water or more; and (5) 35 to 65% by weight of one or more nonionic surfactants having a HLB value of from 6.0 to 10.5.

7. The water-in-oil emulsion cosmetic as claimed in claim 6, wherein said emulsifier is an emulsifier mixture comprising 20 to 30% by weight of said α-monoglyceryl ether represented by said formula (I), 1 to 10% by weight of said polyvalent metal salt of the saturated or unsaturated fatty acid, 10 to 30% by weight of said inorganic salt, and 40 to 60% by weight of said nonionic surfactants.

8. The water-in-oil emulsion cosmetic as claimed in claim 6, wherein said polyvalent metal salt is at least one salt selected from the group consisting of calcium, magnesium, zinc and aluminum salts.

9. The water-in-oil emulsion cosmetic as claimed in claim 6, wherein said inorganic salt is at least one salt selected from the group consisting of magnesium sulfate, potassium sulfate, sodium sulfate, aluminum sulfate, magnesium nitrate, potassium nitrate, sodium nitrate, aluminum nitrate, magnesium chloride, potassium chloride, sodium chloride and aluminum chloride.

10. The water-in-oil emulsion cosmetic as claimed in claim 6, wherein said oily base further contains at least one compound selected from the group consisting of hydrocarbons, waxes, esters, natural animal and vegetable fats and oils and diglycerides.

* * * * *